(12) United States Patent
Sharma et al.

(10) Patent No.: US 10,987,415 B2
(45) Date of Patent: Apr. 27, 2021

(54) PROCESS FOR PRODUCTION OF PURIFIED RECOMBINANT CHOLERA TOXIN B (RCTB) AND FORMULATION THEREON

(71) Applicant: MSD WELLCOME TRUST HILLEMAN LABORATORIES PVT. LTD., New Delhi (IN)

(72) Inventors: Tarun Sharma, New Delhi (IN); Neeraj Joshi, New Delhi (IN); Vibhu Kanchan, New Delhi (IN); Deepa Sikriwal, New Delhi (IN); Nidhi Shukla, Ghaziabad (IN); Davinder Gill, New Delhi (IN)

(73) Assignee: MSD WELLCOME TRUST HILLEMAN LABORATORIES PVT. LTD., New Delhi (IN)

( * ) Notice: Subject to any disclaimer, the term of this patent is extended or adjusted under 35 U.S.C. 154(b) by 0 days.

(21) Appl. No.: 16/061,853

(22) PCT Filed: Dec. 9, 2016

(86) PCT No.: PCT/IB2016/057460
§ 371 (c)(1),
(2) Date: Jun. 13, 2018

(87) PCT Pub. No.: WO2017/103748
PCT Pub. Date: Jun. 22, 2017

(65) Prior Publication Data
US 2018/0360944 A1    Dec. 20, 2018

(30) Foreign Application Priority Data
Dec. 14, 2015   (IN) .......................... 4089/DEL/2015

(51) Int. Cl.
| | | |
|---|---|---|
| C12N 1/00 | (2006.01) |
| A61K 39/106 | (2006.01) |
| A01N 65/00 | (2009.01) |
| A01N 63/00 | (2020.01) |
| A61K 39/02 | (2006.01) |
| C07K 14/28 | (2006.01) |
| C12P 21/02 | (2006.01) |
| A61P 31/04 | (2006.01) |
| C12P 1/04 | (2006.01) |
| A61K 39/00 | (2006.01) |
| C12N 15/86 | (2006.01) |
| C12N 1/20 | (2006.01) |

(52) U.S. Cl.
CPC ............ *A61K 39/107* (2013.01); *A61P 31/04* (2018.01); *C07K 14/28* (2013.01); *C12P 1/04* (2013.01); *C12P 21/02* (2013.01); *A61K 2039/521* (2013.01); *C12N 1/20* (2013.01); *C12N 15/86* (2013.01)

(58) Field of Classification Search
CPC .................................................. A61K 39/107
See application file for complete search history.

(56) References Cited

U.S. PATENT DOCUMENTS 4,264,737 A * 4/1981 Murphy ............... A61K 39/107
                                                  435/444
2015/0071994 A1* 3/2015 Schentag ............ A61K 9/4891
                                                  424/452

OTHER PUBLICATIONS

Lebens et al., Bio-Technology, 1994; 11(13):1574-1578 (Year: 1994).*
Lindquist, Department of Bacteriology, U.W.-Madison; Differential Media: Glucose Fermentation Broth, https://www.jlindquist.com/generalmicro/dfnewgfbpage.html, last modified Jun. 20, 2005 (Year: 2005).*

* cited by examiner

*Primary Examiner* — Gary B Nickol
*Assistant Examiner* — Lakia J Jackson-Tongue
(74) *Attorney, Agent, or Firm* — W&C IP

(57) ABSTRACT

The present invention relates to a novel process of production of purified recombinant cholera toxin B (rCTB) which provides protection against diarrhea caused by various bacteria such as *Vibrio cholerae* and Enterotoxigenic *Escherichia coli* (ETEC). More particularly, the present invention relates to a process of production of rCTB with significantly higher yield and higher purity. The present invention also relates to a vaccine formulation having synergistic protection against *Vibrio cholerae* and cross protection against ETEC.

10 Claims, 7 Drawing Sheets

(A) Lane No's

| Lane. No. | Sample |
|---|---|
| 1 | Marker |
| 2 | Harvest before Heat – 10µl |
| 3 | Harvest after Heat – 10µl |
| 4 | rCTB before 10 kd TFF – 10 µl |
| 5 | rCTB before 10 kd TFF (Dil. 1:4) – 2µl |
| 6 | rCTB after 10 kd TFF – 10 µl |
| 7 | rCTB after 10 kd TFF (Dil. 1:4) – 2 µl |

(B) Lane No's

| Lane. No. | Sample |
|---|---|
| 1 | Marker |
| 2 | rCTB Std. – 2µl |
| 3 | Run 1 – 2µl |
| 4 | Run 2 – 2 µl |
| 5 | Run 3 – 2µl |

PROCESS FOR PRODUCTION OF PURIFIED RECOMBINANT CHOLERA TOXIN B (RCTB) AND FORMULATION THEREON

FIELD OF THE INVENTION

The present invention relates to a novel process for production of purified recombinant cholera toxin B (rCTB) which provides protection against diarrhea caused by various bacteria such as *Vibrio cholerae* and Enterotoxigenic *Escherichia coli* (ETEC). More particularly, the present invention relates to a process for production of rCTB with significantly higher yield and higher purity. The present invention also discloses the vaccine formulation of purified rCTB against *Vibrio cholerae* and Enterotoxigenic *Escherichia coli* (ETEC) having synergistic effect when formulated along with whole cell inactivated Cholera strain.

BACKGROUND OF THE INVENTION

Diarrheal diseases are constant global threat to public health. Major causes of diarrhea include certain bacteria, viruses or parasites, food intolerances etc. One of the major causes of infant and adult diarrhea is *Vibrio cholerae*.

*Vibrio cholerae* is a gram negative bacterium which colonizes the small intestine without invading the epithelium and causes an acute intestinal cholera infection. Although, more than 200 serogroups of *Vibrio cholerae* have been identified, most cases of cholera are caused by two serogoups, O1 and O139. The disease is caused when *Vibrio cholerae* bacteria are ingested through contaminated food or drinking water. Cholera, which affects only humans, is mediated by cholera toxin (CT), which is secreted by *Vibrio Cholera* in the intestine and acts upon the mucosal cells of the gut, causing a copious, painless, watery diarrhea that can lead to severe dehydration and shock. If it is left untreated, death can occur within hours. It is estimated that a mortality of 2,8,000 to 1,42,000 and a morbidity of 1.4 to 4.3 million annual cases can be attributed to Cholera. It occurs as an epidemic due to natural or man-made catastrophe, and is also endemic in many developing countries. In such disasters and in endemic countries, clean drinking water and proper sanitation is unavailable and therefore the intervention of vaccines becomes essential. In 2010, the WHO recommended the use of oral cholera vaccines along with other control measures, both in endemic countries and for cholera epidemics [Cholera-fact sheet N107. World Health Organization. 2012, pp. Cholera-fact sheet N107]

There are three WHO pre-qualified killed oral cholera vaccines currently available:
1. Dukoral® containing whole-cell components and recombinant cholera toxin B-subunit (rCTB); and
2. Shanchol®/Euvichol® which lacks rCTB but contains *Vibrio cholerae* strains of the O139 serogroup in addition to the O1 serogroup.

It is well known that killed whole cell vaccine containing rCTB provides better protection than the killed whole cell vaccine without rCTB. Due to the cross-reactivity of anti-CTB antibodies to heat labile enterotoxin (LTB), killed whole cell vaccine containing rCTB (Dukoral) is also effective against Enterotoxigenic *Escherichia coli* (ETEC) [0 Lucas M. E, Deen J. L, Von Seidlein L, Wang X. Y, Ampuero J, Puri M, Ali M, Ansaruzzaman M, Amos J, Macuamule A, et al. 'Effectiveness of mass oral cholera vaccination in Beira, Mozambique.' N. Engl. J. Med. 2005, 352, 757-7671]. Shanchol lacks the rCTB component and therefore lacks the benefits such as short term ETEC cross protection, synergistic protective effect (anti-bacterial+anti toxic immunity), early and long term protection etc. Therefore, it is better to include rCTB in oral cholera vaccines.

The rCTB is acid-labile so the Dukoral vaccine has to be administered with 75-150 mL of bicarbonate buffer prior to the administration of vaccine which makes the administration logistically difficult for children below 5 years of age and even for adults. Also, in Dukoral the said buffer sachet has to be opened and the contents are to be dissolved in requisite amount of water following addition and mixing of the vaccine from the glass vial. This additional dose preparation steps makes the vaccine in convenient and cumbersome to use.

The addition of rCTB in the oral cholera vaccine can lead to an increase in the cost of the vaccine as is clearly evident from Dukoral/Shanchol comparison where Dukoral is priced at more than $45 per dose and Shanchol priced at $5 per dose. One of the ways in which the oral cholera vaccine comprising rCTB can be made cost effective is by developing such a process for rCTB fermentation and purification which gives high culture OD and high rCTB yield using an easy and efficient purification method.

There are number of patents and non-patents disclosures relating to the production and purification of rCTB. Non-patent disclosure in the article, 'Recombinant system for overexpression of cholera toxin B subunit in *Vibrio cholerae* as a basis for vaccine development', PNAS, 1989, Vol 86, Pg 481-485, discloses that the best yield obtained by using affinity chromatography columns was 75 ug/ml which is not at all cost effective from production point of view. Another non patent titled, 'Cholera Toxin B: One Subunit with Many Pharmaceutical Applications,' Toxins 2015, 7, 974-996, disclosed an exhaustive list of mode of expression systems used for rCTB production till date and the purification methods used. This data show that yield of more than 1 gm/Lt of rCTB has not been achieved till now.

In view of the above prior arts, a real contribution in this field would be to develop a process of production and purification for recombinant cholera toxin B which results into a significantly higher yield along with high purity. Also, there is a need to develop a formulation and a dosage form which is thermostable, eliminates the need for buffer administration and make the vaccine delivery easy.

OBJECT OF THE INVENTION

The main object of the present invention is to provide a novel process for production of purified recombinant cholera toxin B (rCTB).

Yet another object of the present invention is to provide a process of fermentation and purification to obtain purified recombinant cholera toxin B (rCTB) with significantly high yield and high purity.

Another object of the present invention is to provide a process for fermentation and purification of rCTB to obtain purified recombinant cholera toxin B (rCTB) while eliminating the undesired impurities in a very short time by simple and efficient methods.

Yet another object of the present invention is to provide a scalable, less time consuming, cost effective, environment-friendly and affordable process for production of purified recombinant cholera toxin B (rCTB)

Yet another object of the present invention is to provide purified recombinant cholera toxin B (rCTB) capable of being used in novel vaccine formulation against *Vibrio cholerae*.

Yet another object of the present invention is to provide a novel vaccine formulation capable of being used in oral cholera vaccine which provides an early, long term and synergistic protection against *Vibrio cholerae* and cross protection against ETEC.

SUMMARY OF THE INVENTION

Accordingly, the present invention provides a novel process for production of purified recombinant cholera toxin B (rCTB) with significantly higher yield and higher purity. The present process for production of rCTB is scalable, less time consuming and environment friendly as the bacterial strains are inactivated within the fermenter and hence, minimum possibility of contaminating the environment.

Present invention also relates to a vaccine formulation of rCTB with killed whole cell *Vibrio cholerae* and the presentation of said formulation in thermostable dosage form suitable for patient compliance.

The process of the present invention is disclosed below as a non-limiting example:

The recombinant O1 *Vibrio cholerae* strain which constitutively or inducibly overexpresses rCTB was made by Professor Jan Holmgren's lab at Gothenberg University, Sweden and is used to prepare master and working cell banks on predefined media.

In the present invention, the said selected strain is subjected to fermentation in a fermenter maintained at predefined conditions. The fermentation media comprises glucose feed and other known production media components. The fermenter is allowed to run for 18-22 hours while maintaining the predetermined pH and temperature. The resultant fermented culture is subjected to inactivation by heating to a predetermined temperature range to obtain harvest comprising of inactivated cells, denatured proteins and rCTB. The harvest is centrifuged at predetermined rpm at room temperature. The resultant supernatant is subjected to acid precipitation and ultrafiltration to yield purified rCTB. The filtrate so obtained is further subjected to diafiltration followed by sterile filtration to yield purified and sterilized rCTB.

The resultant purified and sterilized rCTB is subjected to characterization and quantitation. After confirming the desired purity by HPLC and yield by GM1 ELISA and SDS-PAGE, the purified and sterilised rCTB is used for formulating in the desired dosage form.

The process of present invention used to purify rCTB exhibits a number of advantages over the prior art, such as providing a significant higher yield along with higher purity. It also provides a robust and rapid process of producing and purifying rCTB. The process is cost effective as it reduces number of unit operations and avoids use of expensive column chromatography to purify the rCTB. An additional advantage is that it is industrially scalable. Due to presence of rCTB the said vaccine formulation also provides synergistic protection against *Vibrio cholerae*. When rCTB is formulated along with whole cell inactivated cholera strains, the vaccine formulation provides cross protection against ETEC.

DETAILED DESCRIPTION OF THE INVENTION

Accordingly, the present invention relates to a process for production of recombinant cholera toxin B which gives a high yield in the range of 1.5-2.5 gm/Litre with >95% purity of rCTB. A recombinant *Vibrio cholerae* strain MS1012, which overexpresses the rCTB, was developed by Gotovax AB, Sweden. Said strain was received by Hilleman Labs as part of collaboration between Gotovax AB, Sweden and MSD Wellcome Trust Hilleman Laboratories Pvt. Ltd. Process development, purification, quantitation and characterization of rCTB from said strain have been performed at Hilleman Labs.

Before the preferred embodiment of the present invention is described, it is understood that this invention is not limited to the particular materials described, as they may vary. It is also understood that the terminology used herein is for the purpose of describing the particular embodiment only, and is not intended to limit the scope of the invention in any way.

It must be noted that as used herein, the singular forms "a", "an" and "the" include plural reference unless the context clearly dictates otherwise.

The selected recombinant *Vibrio cholerae* strain MS1012, which overexpresses the rCTB, is cultured on predefined media and incubated overnight at predefined conditions. The said selected strain is then subjected to fermentation for 18-22 hours while maintaining the pH in the range of 7.2 to 7.5 and temperature is in the range of 35 deg C. to 37 deg C. in presence of glucose feed followed by heating the fermented culture to high temperature in the range of 60° C. to 70° C. for 30 mins.

The resultant fermented culture is then subjected to centrifugation to remove the inactivated cells and denatured proteins.

The resultant supernatant is then subjected to ultrafiltration. The filtrate so obtained is ultrafiltered using 500 Kda ultrafiltration membrane. The retentate is discarded and permeate is collected. Permeate so obtained is subjected to acid precipitation in presence of sodium hexametaphosphate. The precipitate obtained is subjected to centrifugation. The supernatant is discarded and the pellets so formed is collected and dissolved in buffer solution, preferably phosphate buffer with pH 7.4. The resultant pellet buffer solution is further subjected to ultrafiltration using 10 Kda membrane to remove media components. The retentate is collected and filter sterilized by 0.22 μm membrane. The resultant purified and sterilized rCTB is subjected to characterization and quantitation of rCTB.

Figure 3:
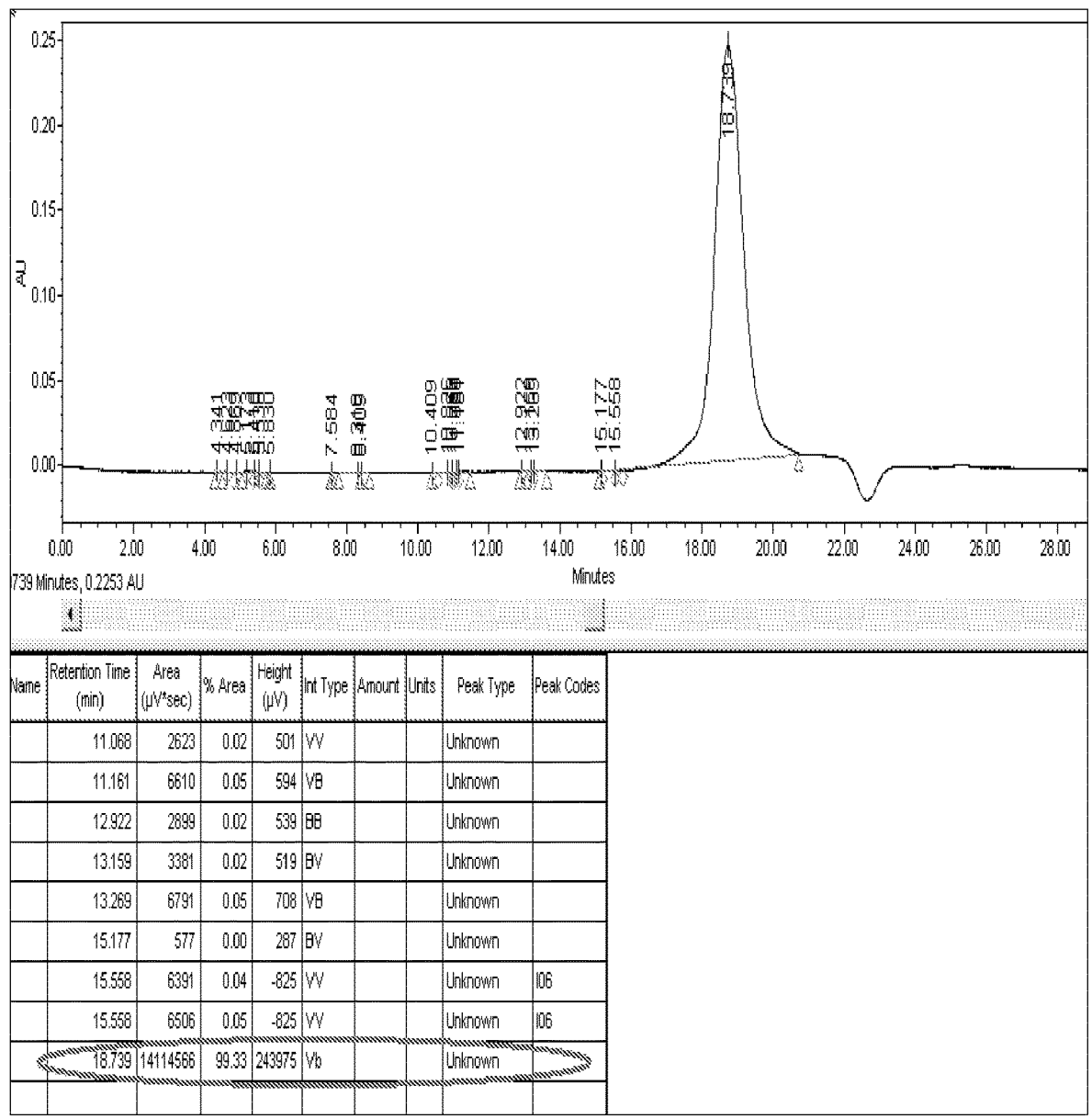
FIG. 3: HPLC Profile of purified rCTB.
Figure 4:
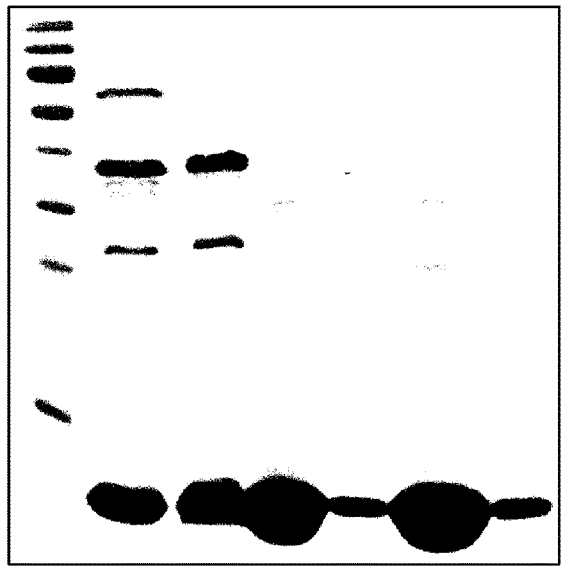
FIG. 4: SDS PAGE of boiled rCTB samples in different stages of purification
Figure 4:
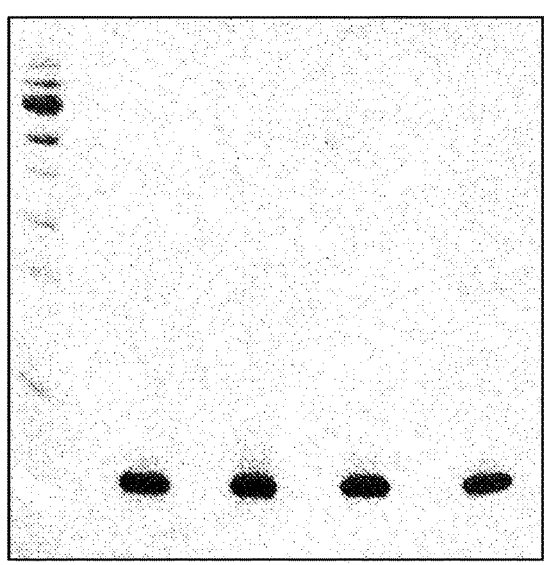

The purity of rCTB is confirmed by HPLC and SDS-PAGE on Novex Tris-Glycine Gels 14%. The HPLC profile (FIG. 3) confirms more than 95% purity.

Further characterization of rCTB is performed by western blot using LT39 monoclonal antibody. Quantitation of rCTB is performed by GM1 ELISA. Both the ELISA and SDS- PAGE densitometry results corroborated each other. The overall yield of rCTB is 1.5 to 2.5 gm/Litre.

After achieving the desired purity and yield, the purified and filter sterilised rCTB is subjected to the formulation step.

The purified rCTB is mixed with inactivated whole cell O1 *Vibrio cholerae* strain naturally isolated with either Ogawa Inaba serotype or recombinantly produced Hikojima strain which co-expresses Ogawa and Inaba to give 1 mg rCTB per 1.5 ml inactivated *Vibrio cholerae* bacteria suspension. The resulting suspension is freeze-dried in vial or tray in the presence of sucrose. Freeze drying cycle is 28 hrs. The shelf temperature is maintained in the range of 30° C. to 50° C., while maintaining the pressure control simultaneously. Freeze dried material is transferred from tray to air tight container in nitrogen chamber and stored at 4° C. until usage.

The resultant freeze dried material can be formulated into the desired dosage form, more preferably tablets. The rCTB is combined with killed whole cell *Vibrio cholerae* and formulated as tablets enteric coated with a protective acid resistant polymer that dissolves and releases rCTB & inactivated whole cell *Vibrio cholerae* specifically in less acidic regions of the GI tract (small intestine). The enteric coating allows the release the rCTB in the small intestine while protecting from the stomach acid environment irrespective of fed or fasting state. The formulation is designed and packaged and marketed in a solid dosage form in blister/strip packing, for travellers or for subjects in cholera endemic or epidemic area above 5 years of age.

Figure 8:
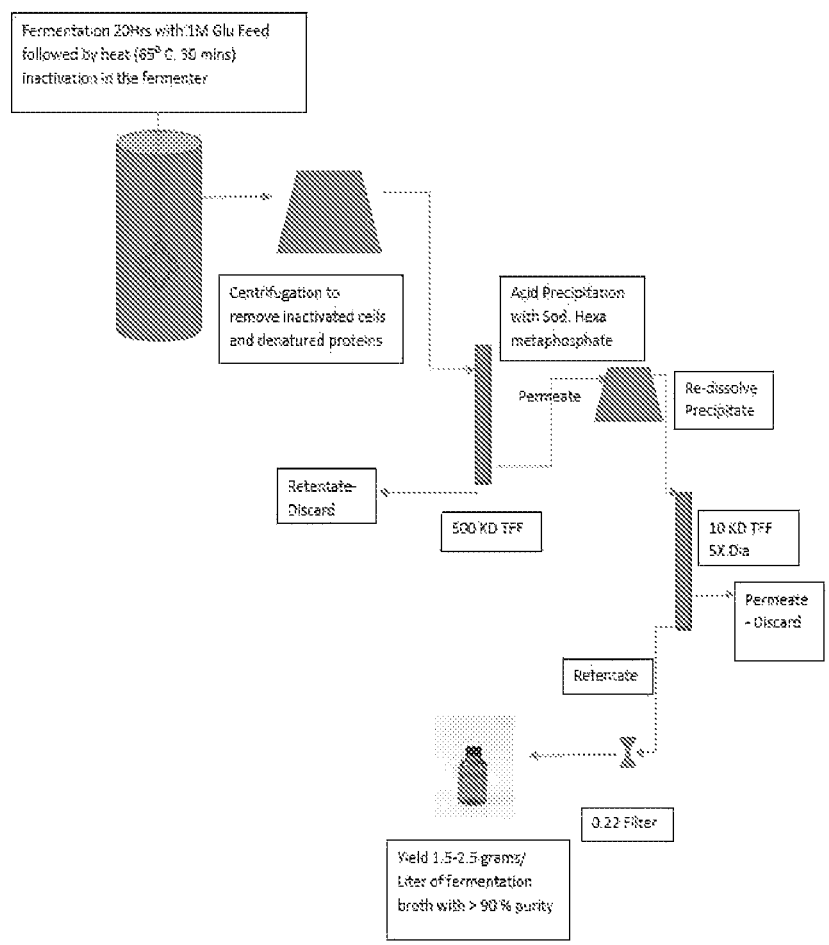
FIG. 8: Schematic diagram for fermentation and purification

Therefore, the present invention provides a significant high yield along with high purity. The process is cost effective as it reduces the total time and avoids use of expensive chromatography matrix required to purify the rCTB. The present invention also provides a novel vaccine formulation in dosage form preferably solid dosage form, more preferably in the form of the tablets, providing cross protection against ETEC and synergistic effect against *Vibrio cholera*. A schematic diagram for fermentation and purification is as shown in FIG. 8.

The above detailed description of process is illustrated by non-limiting examples:

Example 1: Fermentation and Purification of Recombinant Cholera Toxin B (rCTB)

MS 1012 strain is revived from working seed lot on 1.5% agar plates of media like Luria Bertini, MS medium (Casamino acids, 20 gm; Sucrose, 2.5 gm; Na2HPO4.2H2O, 6.27 gm; K2HPO4, 5 gm; NH4Cl, 1 gm; Na2SO4, 0.089 gm; MgCl2.6H2O, 42 mg; MnCl2.4H2O, 4 mg; FeCl3.61H2O, 5 mg), VCG media (Casamino acids, 30 gm; Yeast Extract, MgSO4.7H2O, 0.02 gm; L-Tryptophan, 0.05 gm; KH2PO4, 0.13 gm; Na2HPO4.2H2O, 0.87 gm; Sucrose, 3.4 gm), rCTB production media (Casamino acids, 30 gm; Sucrose, 2.5 gm; Na2HPO4.2H2O, 6.27 gm; K2HPO4, 5 gm; NH4Cl, 1 gm; Na2SO4, 0.089 gm; MgCl2.6H2O, 42 mg; MnCl2.4H2O, 4 mg; FeCl3.6H2O, 5 mg) etc and incubated overnight at 37° C.

Figure 1:
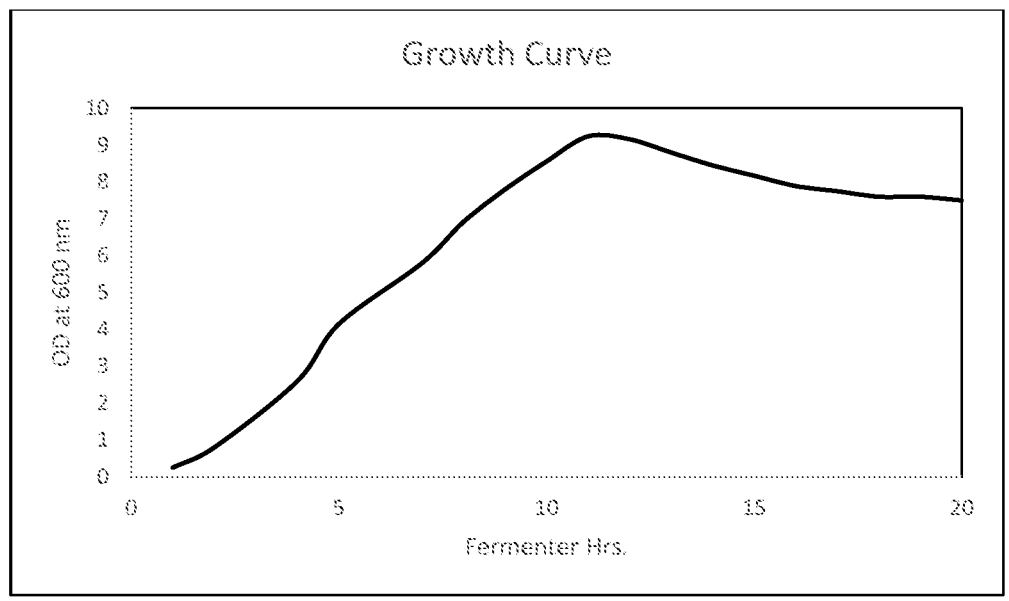
FIG. 1: Growth curve of the strain MS1012 during fermentation.
Figure 2:
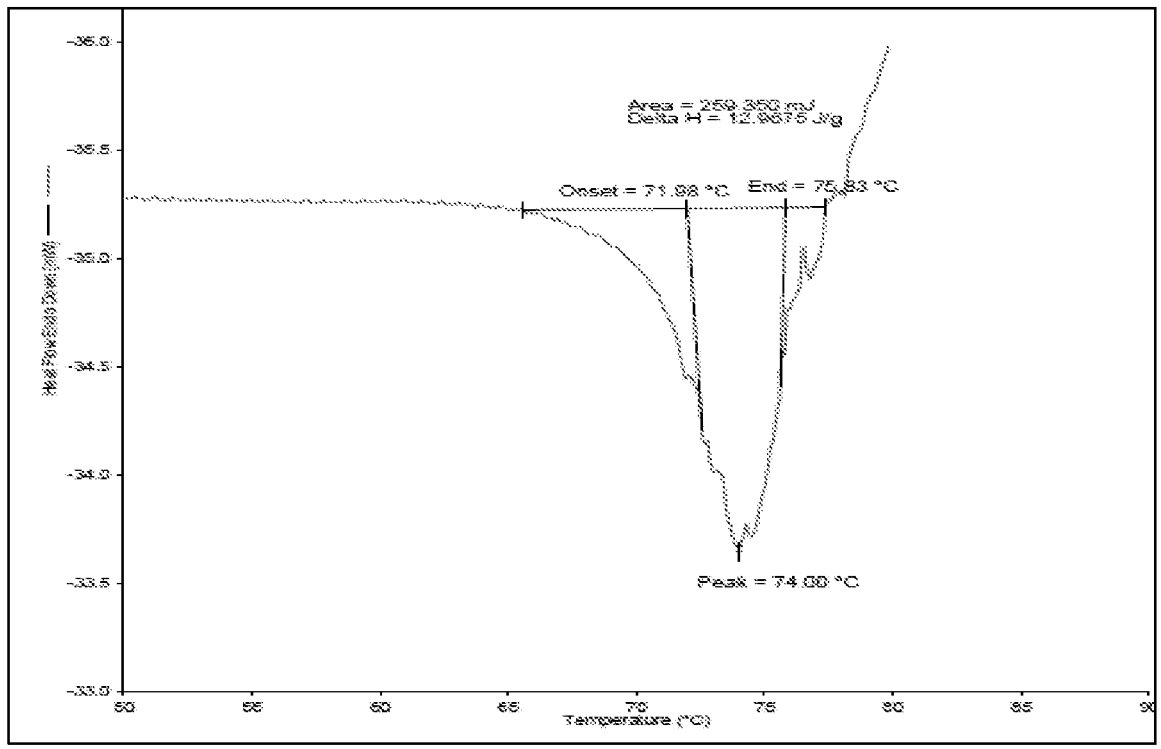
FIG. 2: Differential scanning calorimetry (DCS) of rCTB.

From this plate, 3 colonies are transferred into 35 ml of media like Luria Bertini, MS medium, VCG media, rCTB production media etc and the cultures are grown at 37° C. with shaking (180 rpm) up to an OD600 from 0.9-1.5/ml or mid-log phase. 35 ml of this culture is used to inoculate 2.5 litre of rCTB production medium containing Casamino acids, 30 gm; Sucrose, 2.5 gm; Na2HPO4.2H2O, 6.27 gm; K2HPO4, 5 gm; NH4Cl, 1 gm; Na2SO4, 0.089 gm; MgCl2.6H2O, 42 mg; MnCl2.4H2O, 4 mg; FeCl3.6H2O, 5 mg; in a 5 litre fermenter. pH of the fermenter is maintained in the range of 7.2±1 to 7.4±1, temperature at 37° C. aeration of 2 reactor volumes/min, stirring at 600 rpm and a feed containing 1M glucose & rCTB production media is given at a feed rate of 0.3 ml/min after 5 hrs of fermentation when pO2 drops less than 30%. The fermentation culture of strain MS1012 reached an OD600 of 8-10 in 10-12 hrs (FIG. 1). Antifoam 204 (Sigma) diluted to 30% in water is used to control foaming. The culture is aborted after 20 hrs and the temperature of the fermenter is increased to 65° C. for 30 mins to precipitate the unwanted bacterial proteins. rCTB is resistant to heat denaturation till 74° C. and therefore does not get precipitated (DSC, FIG. 2) The heat treated fermented culture is centrifuged at 8000 rpm at room temperature for 90 mins. The debris is discarded and supernatant is collected which is then subjected to 500 Kda tangential flow filtration (TFF), retentate is discarded and the permeate is collected. Permeate is subjected to acid precipitation using 6M HCl followed by 3M HCl till the p1-1 reaches 4.5, in the presence of sodium hexametaphosphate at a concentration of 2.5 gm/lt. This acid treated 500 Kda permeate is centrifuged at 8000 rpm at 2-8° C. for 60 min. Supernatant is discarded and the pellet is dissolved in 500-600 ml of 20 mM phosphate buffer, pH 7.4 which is then subjected to 5×10 Kda TFF to remove the sodium hexametaphosphate and media components from the pellet. The retentate is collected, filtered and then sterilized by 0.22 micron filter.

This is the purified and sterilized rCTB. The fermentation and purification process is performed as shown in the schematic diagram as given above. Three consistency runs for rCTB fermentation and purification are done by the process described above.

Example 2: Purity, Characterization & Quantitation of Recombinant Cholera Toxin B The purity of rCTB is confirmed by HPLC and SDS-PAGE. Samples are analysed by HPLC-SEC on a TSKgel 5000 PWXL (7.8×300 mm, particle size 7 µm, TOSOH) and TSKgel 4000 PWXL (7.8×300 mm, particle size 7 µm, TOSOH) in series with TSKgel PWXL guard column (6.0× 40 mm, TOSOH). The mobile phase is 0.1 M NaNo3, pH 7.2, at the flow rate of 1.0 ml/min in isocratic mode for 30 min. Void and total column volume are determined with dextran, MW 50, 00,000-400, 00,000 (HIMEDIA) and deuterium oxide (D2O, Merck), respectively. Protein peaks are detected at 280 nm. The HPLC profile (FIG. 3) showed that this purification process gave us >95% pure rCTB.

Figures 5A, 5B:
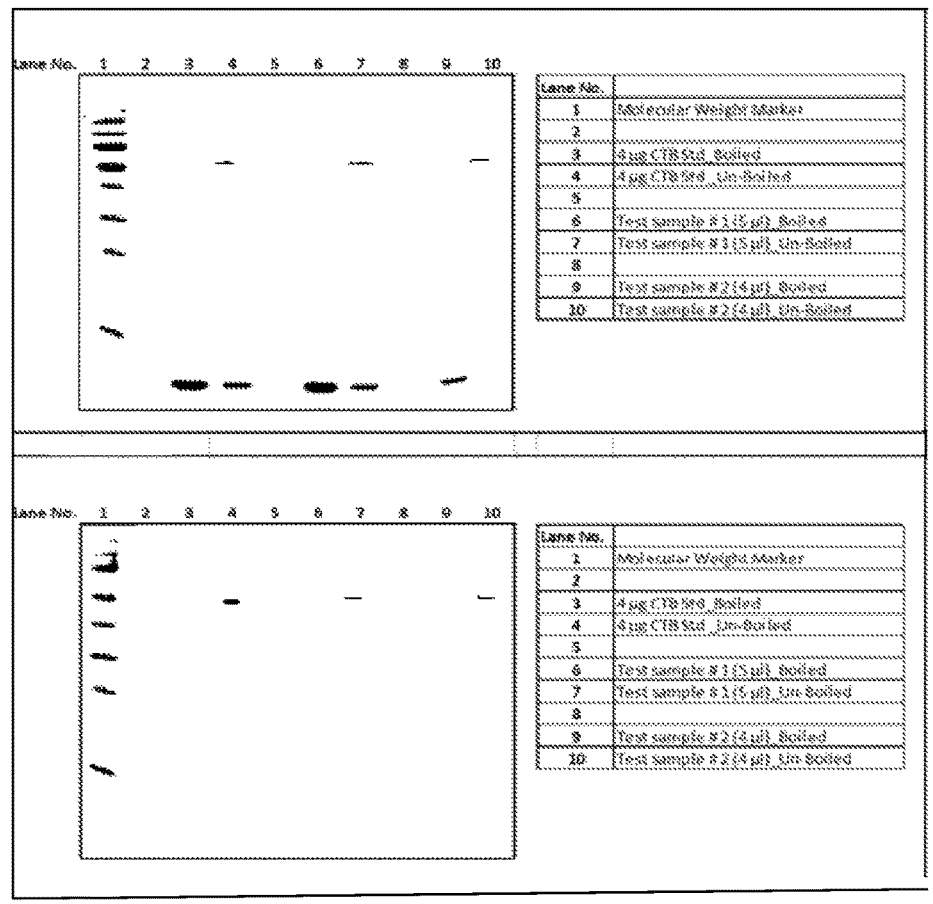
FIG. 5: (A) SDS-PAGE of boiled and un-boiled samples of rCTB. (B) Western blot of rCTB.

The purified rCTB is also checked by SDS-PAGE on Novex Tris-Glycine Gels 14% and detection of the bands is done using Gel Doc Imager (FIGS. 5A & B). The gel clearly shows presence of only one major band at 12 Kda (FIG. 5B). The results of rCTB purity are completely in agreement with the EMEA specifications as shown in Table 1 for rCTB below.

TABLE 1

| EMEA specifications for recombinant cholera toxin | | |
|---|---|---|
| Test attribute | Test method | Specification |
| Physical appearance | Visual inspection | Clear, colourless to weakly yellow solution. Some particles may occur. |

TABLE 1-continued

EMEA specifications for recombinant cholera toxin

| Test attribute | Test method | Specification |
|---|---|---|
| Identification | Ouchterlony immunoelectro-phoresis | Immunological identity with rCTB and CTB |
| pH | Potentiometry | 7.0-7.6 |
| Antigen concentration | Mancini | >1 mg rCTB/ml |
| Protein content | Kjeldahl | >1 mg protein/ml |
| Antigenic purity | Antigen content/ protein content | NLT 0.8 mg rCTB/mg protein |
| Purity | RP-HPLC | <10% unrelated proteins |
| Purity | SDS-PAGE | Not more than 2 bands visible; one major at 12 kD and one minor if present at 23 kD |
| Purity | SE-HPLC | Area of pentamer peak >90% of integrated area. |
| Sterility | Ph Eur Membrane filtration | Sterile |

Characterization of rCTB is done by western blot using LT39 monoclonal antibody at a dilution of 1:100 dilution and Goat anti-mouse IgG-HRP at a dilution of 1:2000. For the western blot, both boiled and un-boiled samples are run in SDS-PAGE. Boiling breaks, the 60 Kda pentamer rCTB into 12 Kda monomers. As the western blot antibody recognizes only pentamer, only the band for pentamer at 60 KDa in the western blot is observed and no band for the monomer (FIG. 5 (B))

Figure 6:
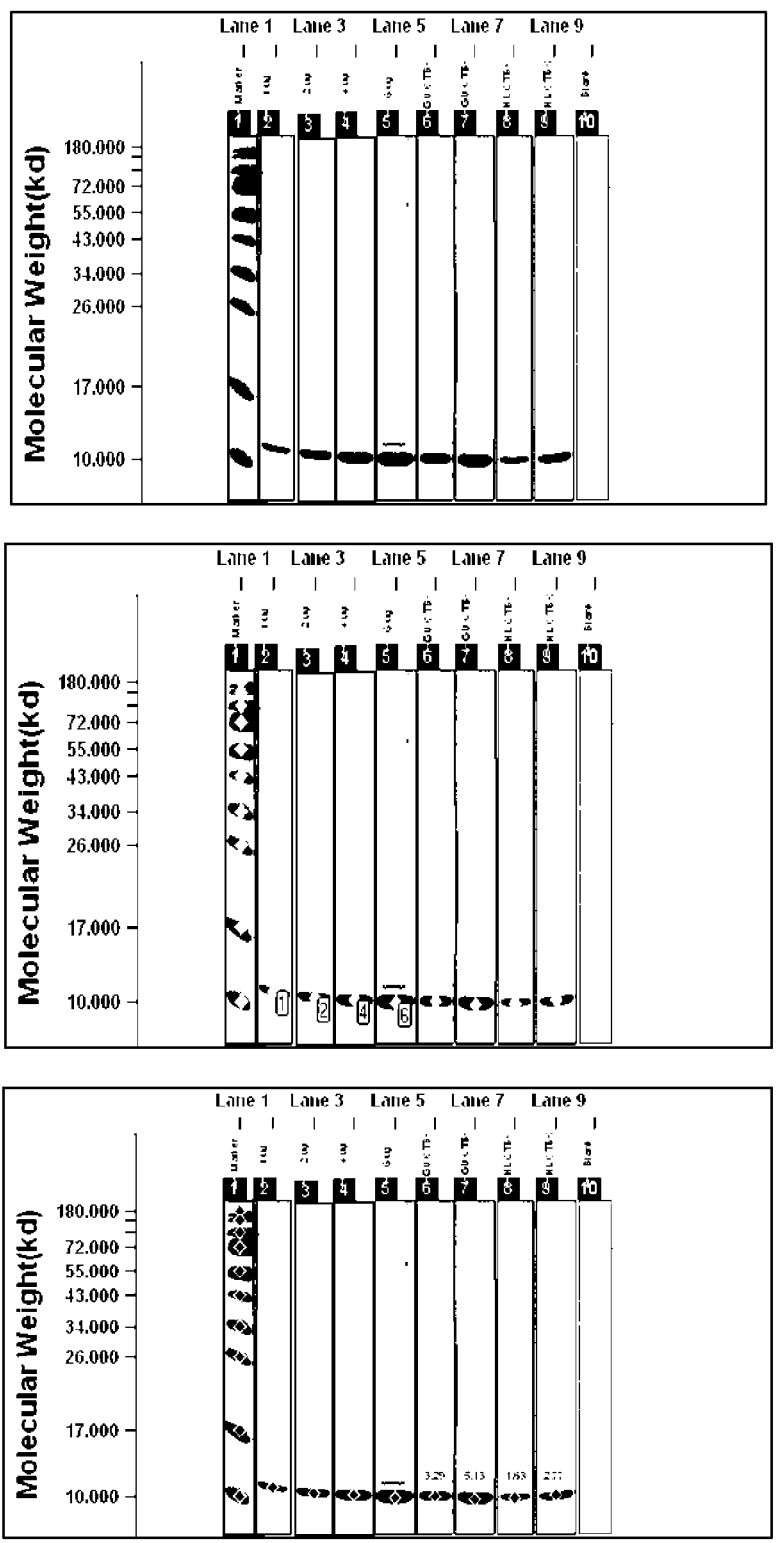
FIG. 6: Densitometry results done for quantitation of rCTB.
Figure 7:
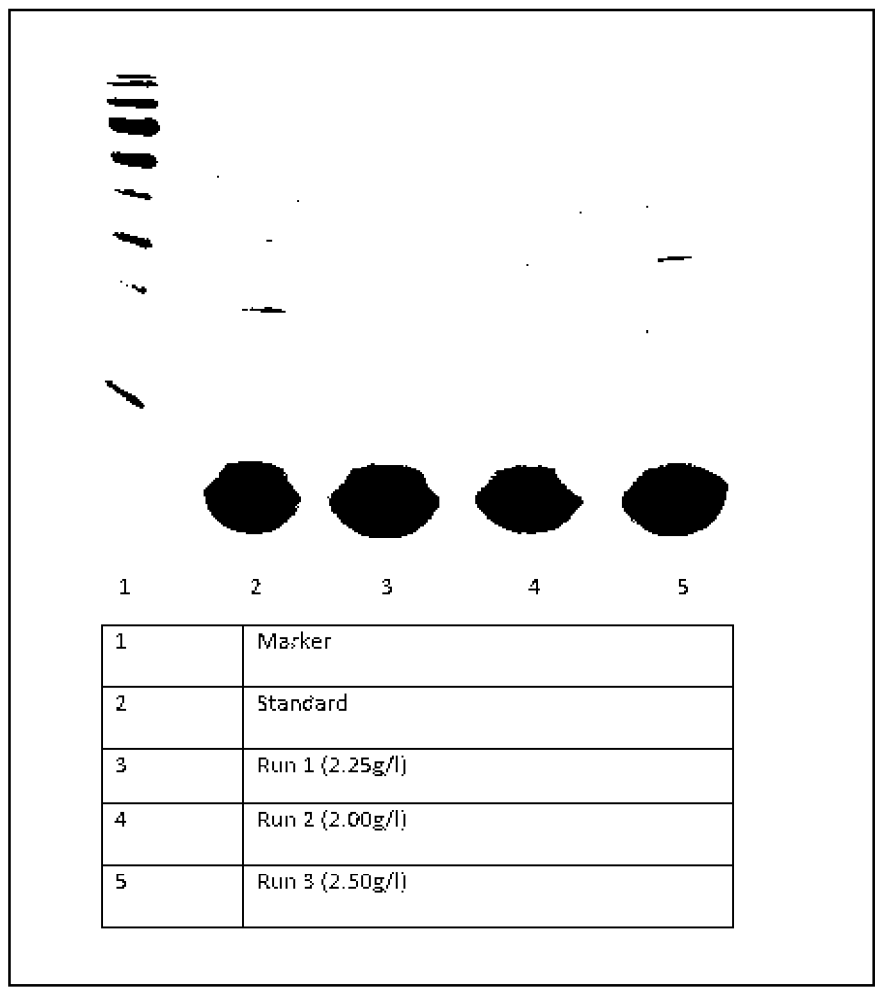
FIG. 7: SDS PAGE for Consistency runs of rCTB fermentation and purification batches

Quantitation of rCTB is done by GM1 ELISA as described earlier [Identification of *Escherichia coli* heat-labile enterotoxin by means of a ganglioside immunosorbent assay (GM1-ELISA) procedure. Curr. Microbio. 1978; 1: 19-23]. Briefly, 0.3 nmol/ml of GM1 is coated on ELISA plate. Three fold dilutions of samples are made. Purified CTB at a concentration of 0.5 ug/ml, is used as a reference. LT39 monoclonal antibody is used as primary antibody at a dilution of 1:100 dilutions. Goat anti-mouse IgG-HRP is used as a secondary antibody at a dilution of 1:4000. Quantitation of rCTB is also done by densitometry, the result of which is shown in FIG. 6. Both the ELISA and densitometry results corroborated each other. The overall yield of rCTB is 1.5 to 2.5 gm/Litre. In the three consistency runs the yield of rCTB is 2 gm/L, 1.7 gm/L and 2.25 gm/L (FIG. 7)

Example 3: Formulation and Target Product Profile (TPP)

Formulations of formalin-killed whole cell *Vibrio cholerae* bacteria and rCTB (1 mg per 1.5 ml formalin-killed *Vibrio cholerae* bacteria) are freeze-dried in the presence of Sucrose (2.5 mg/ml). Freeze drying cycle is 28 hrs. The shelf temperature is set to 40° C. and the pressure control to 922 mbar. Freeze dried material is transferred from tray to air tight container in nitrogen chamber and stored at 4° C. until usage. The TPP of this formulation is tablet. One tablet of vaccine contained an active pharmaceutical compound of heat-killed whole cells of *Vibrio cholerae* and rCTB (100-150 mg per tablet). The excipients used in tablet are micro crystalline cellulose (25%-30%), Starch (25%-30%), Mg stearate (0.5%-0.7%), colloidal silicone dioxide (0.5%-1%). Mixture of all ingredients is directly compressed in a tablet press. Tablets are seal coated with OPA dry (3-5%) and finally enteric coated with EUDRAGITL30D55/Acryl-EZEII (8-12%)(a water dispersible enteric film coating for solid dosage forms such as tablets available from Colorcon North America and other outlets).

We claim:

1. A novel process for producing purified recombinant cholera toxin B (rCTB) from *Vibrio cholerae* and formulating the purified rCtB to obtain a novel vaccine formulation, said process comprising the steps of
fermentating an rCTB producing *Vibrio cholerae* strain to obtain a fermented culture;
heat inactivating the fermented culture to obtain a harvest of partially purified rCTB;
purifying said harvest to obtain purified rCTB; and
formulating the purified rCTB to produce the novel vaccine formulation,
wherein said fermented culture is subjected to a step of heat inactivating at a temperature range of 65° C.±5° C. for 30±15 mins, followed by centrifugation to pellet out inactivated cells and denatured contaminating proteins; wherein the post centrifugation supernatant contains more than 70% pure rCTB, and wherein this partially purified rCTB is further purified by precipitation and tangential flow filtration to yield more than 90-95% pure rCTB.

2. The process as claimed in claim 1 wherein said yields are in the range of 1.5-2.5 gm/litre and purity of the purified, rCTB is higher than 95% (>95%).

3. The process as claimed in claim 1 wherein said fermentation step comprises of following steps:
(a) inoculating an rCTB producing *Vibrio cholerae* strain into rCTB production media in a fermenter at pre-defined conditions;
(b) running the fermenter at a predetermined pH and a predetermined temperature for a predetermined duration of time to obtain the fermented culture.

4. The process as claimed in claim 3 wherein said predefined conditions include addition of feed containing 1M glucose to the fermenter media.

5. The process as claimed in claim 3 wherein said predetermined pH is in the range of 7.2-7.5, said predetermined temperature is in the range of 35–37° C., and said predetermined duration of time ranges from 18-22 hrs.

6. A novel process for producing purified recombinant cholera toxin B (rCTB) from *Vibrio cholerae* and formulating the purified rCtB to obtain a novel vaccine formulation, said process comprising the steps of
fermentating an rCTB producing *Vibrio cholerae* strain to obtain a fermented culture;
heat inactivating the fermented culture to obtain a harvest of partially purified rCTB;
purifying said harvest to obtain purified rCTB; and
formulating the purified rCTB to produce the novel vaccine formulation, wherein the purifying step is performed without chromatography, wherein said fermented culture is subjected to a step of heat inactivating at a temperature range of 65° C.±5° C. for 30±15 mins, followed by centrifugation to pellet out inactivated cells and denatured contaminating proteins; wherein the post centrifugation supernatant contains more than 70% pure rCTB, and wherein this partially purified rCTB is further purified by precipitation and tangential flow filtration to yield more than 90-95% pure rCTB.

7. The process as claimed in claim 6 wherein said yields are in the range of 1.5-2.5 gm/litre and purity of the purified, rCTB is higher than 95% (>95%).

8. The process as claimed in claim 6 wherein said fermentation step comprises of following steps:

(c) inoculating an rCTB producing *Vibrio cholerae* strain into rCTB production media in a fermenter at predefined conditions;

(d) running the fermenter at a predetermined pH and a predetermined temperature for a predetermined duration of time to obtain the fermented culture.

9. The process as claimed in claim 8 wherein said predefined conditions include addition of feed containing 1M glucose to the fermenter media.

10. The process as claimed in claim 8 wherein said predetermined pH is in the range of 7.2-7.5, said predetermined temperature is in the range of 35–37° C., and said predetermined duration of time ranges from 18-22 hrs.

* * * * *